United States Patent
Xu et al.

(10) Patent No.: US 8,158,402 B2
(45) Date of Patent: Apr. 17, 2012

(54) **ACETOIN HIGH-YIELD *BACILLUS PUMILUS* STRAIN**

(75) Inventors: Ping Xu, Shanghai (CN); Zijun Xiao, Shanghai (CN); Yi Du, Shanghai (CN); Zhonghao Wei, Shanghai (CN)

(73) Assignee: Shanghai Apple Flavor & Fragrance Co., Ltd., Shanghai (CN)

( * ) Notice: Subject to any disclaimer, the term of this patent is extended or adjusted under 35 U.S.C. 154(b) by 874 days.

(21) Appl. No.: 11/667,567

(22) PCT Filed: Nov. 4, 2005

(86) PCT No.: PCT/CN2005/001849
§ 371 (c)(1),
(2), (4) Date: Sep. 25, 2008

(87) PCT Pub. No.: WO2006/053480
PCT Pub. Date: May 26, 2006

(65) Prior Publication Data
US 2009/0215152 A1    Aug. 27, 2009

(51) Int. Cl.
*C12N 1/20* (2006.01)
*C12P 7/26* (2006.01)
*C12P 1/00* (2006.01)

(52) U.S. Cl. .................. 435/252.5; 435/148; 435/41

(58) Field of Classification Search .................. None
See application file for complete search history.

(56) References Cited

FOREIGN PATENT DOCUMENTS

EP    0 430 406 A2    9/1990
EP    0 372 332 A2    6/1993

OTHER PUBLICATIONS

Lovett et al. Identification of *Bacillus subtilis* NRRL B-3275 as a strain of *Bacillus pumilus*. J Bacteriol. Nov. 1969;100(2):658-61.*
Xiao et al. Acetoin production associated with the increase of cell biomass in *Bacillus pumilus* ATCC 14884. African Journal of Microbiology Research vol. 4(19), pp. 1997-2003, Oct. 4, 2010.*
PCT International Search Report for Appln. No. PCT/CN2005/001849 mailed Feb. 16, 2006.

* cited by examiner

*Primary Examiner* — Yong Pak
(74) *Attorney, Agent, or Firm* — Finnegan, Henderson, Farabow, Garrett & Dunner, LLP

(57) ABSTRACT

A high-yield bacterial strain for producing acetoin named *Bacillus pumilus* XH195 has been deposited in a microorganism deposit center in Germany. The deposit number is DSM 16187. The bacteria of the strain are rod-shaped, 1.5 μm to 3.0 μm in length, and 0.6 μm to 0.7 μm in diameter. The colony color of the bacterial strain is yellow or white. The strain has the typical fatty acid profile of *Bacillus* and its physiological and biochemical characteristics align with those of *Bacillus pumilus*. When the bacteria of strain were cultured at 37° C. for 60 hours with shaking, the yield of acetoin could reach 63.0 g/L or 58.1 g/L, when glucose or sucrose was used as the substrate, respectively.

17 Claims, 2 Drawing Sheets

ACETOIN HIGH-YIELD *BACILLUS PUMILUS* STRAIN

CROSS REFERENCE TO RELATED APPLICATIONS

This application claims the benefit of PCT Application No. PCT/CN2005/001849, filed Apr. 11, 2005, which is incorporated herein by reference.

FIELD OF THE INVENTION

This invention relates to the field of biotechnology. In particular it relates to a *Bacillus pumilus* strain, especially a high-yield, acetoin-producing *Bacillus pumilus* strain.

BACKGROUND OF THE INVENTION

Acetoin is a popular food flavoring that is widely used in the world as a component of flavorings of cream, yogurt, strawberry and so on. With a pleasant buttery odor, acetoin is often used to enhance the flavor of cream, cheese, coffee, nut, etc. Acetoin can also change the flavor of beer and cheese during fermentation. Nowadays as the consumption of dairy products continues to grow, more and more people enjoy foods with a cream flavor. Research and development in acetoin production have drawn attention of companies and research institutions throughout the world.

At present, methods for acetoin production in the laboratory mainly include the following: extracting acetoin from acetoin-containing plants; biological methods; oxidizing 2,3-butanedione using catalysts; oxidizing butanone using electrochemical methods; hydrolyzing linear ketones in sulfuric acid dilution using thallium salt; and synthesizing acetoin from butanedione or 2,3-butanediol.

Studies on acetoin production were first reported in the early twentieth century. One method employed was partial deoxidation of 2,3-butanedione using zinc and acids. Another method was selective oxidation of 2,3-butanediol. Recently, many biological techniques for acetoin production have been reported, for example, converting 2,3-butanediol into acetoin with mycoderma, or using *aspergillus, penicillium* or other epiphytes to act on sugarcane juice. But these studies were conducted in laboratory settings. To meet the needs for environmental protection and green technologies, biological methods will be the major direction for future research in acetoin production.

The industrial methods for acetoin production are mainly chemosynthesis using 2,3-butanedione as the substrate. In 1989, Ehime University in Japan successfully obtained acetoin by reducing 2,3-butanedione in the system of Zn—ZnCl-EtOH. In this method, the reaction was carried out with heating and stirring at about 70° C.~80° C. at the natural pressure. Acetoin was obtained after further separation and purification, resulting in a 71% recovery. In 1992, Hangzhou University in China developed a new method to produce acetoin by reduction with NaHSe. In this method, selenium powder was added into a NaHB solution in a stirring reactor. After NaHSe was formed under vacuum, a mixed solution of acetic acid and ethanol, and 2,3-butanedione dissolved in tetrahydrofuran were added into the stirring reactor, where the reaction was carried out at the room temperature. The yield of this method was 57%.

In 1998, Martin Studer et al. of Witwatersrand University used platinum denaturalized by 10,11-dihydrgen *cinchona ledgeriana* (HCD) as a catalyst to selectively deoxidize 2,3-butanedione by hydrogenation. In this method, butanedione, catalyst and HOD in toluene were added into a high-pressure reactor. The reaction pressure was 10.7 Mpa, while the reaction temperature was 0° C.~25° C. The reaction was stopped after about 10 min. The yield of the method was 85%, and some optically active byproducts were also obtained. Since this was a catalytic hydrogenation reaction, controlling the reaction conditions was critical. If the reaction continued, acetoin would be further converted into 2,3-butanediol, and the recovery rate of the acetoin product would only reach 50%. Slipszenko et al. of Hull University also conducted research on butanedione deoxidation by selective catalytic hydrogenation using platinum as the catalyst. But the solvent they used was methylene dichloride, and the reaction pressure, temperature, and yield were 1 Mpa, 5° C.~25° C., and 85%, respectively. In this method, more (R)-acetoin enantiomer could be produced by controlling the reaction time and the hydrogen pressure, and the yield could reach 70%.

Since catalytic hydrogenation is carried out at a high pressure, specific equipments are required. In addition, the catalyst used in the reaction is an expensive precious metal. Problems concerning the catalyst, such as manufacturing, denaturalization, regeneration and metal poisoning, have not been solved and thus confine the method to laboratory studies.

In 1992, Hummel et al. in the United States used enzymes from microorganisms as catalysts for acetoin production. In this method, butanedione reductase is isolated from lactic bacteria or yeast Saccharomycetes, and used to convert butanedione to acetoin in the presence of NADPH at pH 5 and 70° C. The yield of the reaction can reach as high as 100%. Because the enzymes act as stereospecific catalysts, this method produced chiral compounds, generating no or few enantiomers. The advantages of reductases, which are highly selective, high-yield, and safe in food additive production, are obvious. But the key step of this method is to obtain butanedione reductases needed for the reactions. Enzyme-based methods remain a very important research area in the era of green technologies.

Microbial fermentation is an important biological method for acetoin production. The metabolic pathway of acetoin production using glucose or other substrates has been elaborated (FIG. 1), which provides the theoretical basis for fermentative production of acetoin. Although there were some reports including a few patents on this method, most of them were still restricted to laboratory studies. Isolating a high-yield, acetoin-producing bacterial strain is important for fermentative acetoin production. So far, the following strains for acetoin production have been reported: *Klebsiella pneumoniae, Klebsiella oxytoca, Aeromonas hydrophilia, Bacillus subtilis, Bacillus polymyxa, Bacillus licheniformis, Serratia marcescens, Listeria monocytogenes, Aerobacter aerogenes, Bacillus amyloliquefaciens, Enterobacter aerogenes, Lactococcus lactis, Lactobacillus casei, Streptococcus thermophilus, Leuconoctoc mesenteroides, Leuconoctoc lactis, Leuconoctoc oenos, Leuconoctoc pseudomesenteroides, Bacillus stearothermophilus, Hanseniaspora guillieromondil, Saccharomyces carlsbergensis, Saccharomycodes ludwigii, Zygosaccharomyces bailli, Zygosaccharomyces fermentati*, and so on. But all of these strains share the problem that the yield of acetoin is too low, or acetoin is produced only as a by-product of 2,3-butanediol biosynthesis. Therefore, it is difficult to use the strains above for industrial-scale production of acetoin.

Due to the low concentration of acetoin in plants, extracting acetoin from plant materials is costly and not suitable for commercialization. While chemical synthesis can produce high yield acetoin, extreme reaction conditions and sophisticated equipments are required. Moreover, the resulting acetoin is not a natural product and there are serious concerns with environmental protection. The methods of biosynthesis, including microbial fermentation, have been only studied in the laboratories mostly because of low yield of the product, which is caused by problems in the strain used, enzyme activity, optimization of fermentation conditions, or process controls.

SUMMARY

The object of this invention is to provide a high-yield *Bacillus pumilus* for fermentative production of acetoin with glucose or sucrose as the substrate.

The *Bacillus pumilus* strain XH195 in this invention has been deposited in a microorganism deposit center in Germany (Deutsche Sammlung von Mikroorganismen und Zellkulturen GmbH, Braunschweig). The deposit number is DSM 16187.

The bacteria of the *Bacillus pumilus* strain XH195 DSM 16187 are rod-shaped, 1.5 μm to 3.0 μm in length and 0.6 μm to 0.7 μm in diameter, with a colony color of yellow or white (FIG. 2). The bacteria can produce spores and are positive in the VP test. The strain is able to produce acid from glucose, arabinose, xylose, or mannitol, and hydrolyze casein, gelatin, and Tween 80. The strain can utilize citrate, grow in media containing 100 g/L NaCl, and grow at 50° C. The physiological and biochemical characteristics of the strain are described in Table 1.

TABLE 1

Characteristics of the *Bacillus pumilus* strain XH195 DSM 16187

| Characteristics of the strain | Results |
|---|---|
| Rods | + |
| Width | 0.6~0.7 μm |
| Length | 1.5~3.0 μm |
| Spores | + |
| Ellipsoid | + |
| Sporangium | − |
| VP reaction | + |
| pH in VP | 5.0 |
| Acid from glucose | + |
| Acid from arabinose | + |
| Acid from xylose | + |
| Acid from mannitol | + |
| Acid from fructose | + |
| Gas from glucose | − |
| Hydrolysis of casein | + |
| Hydrolysis of gelatin | + |
| Hydrolysis of starch | − |
| Hydrolysis of Tween 80 | + |
| Hydrolysis of esculine | − |
| Utilization of citrate | + |
| Utilization of propionate | − |
| Degradation of tyrosin | − |
| Phenylalanin deaminase | − |
| No$_3$ to NO$_2$ | − |
| Indol | − |
| Growth at pH 5.7 | + |
| Growth with 2% NaCl | + |
| Growth with 5% NaCl | + |
| Growth with 7% NaCl | + |
| Growth with 10% NaCl | + |
| Growth at 45° C. | + |
| Growth at 50° C. | + |
| Growth at 55° C. | − |
| Growth with 0.001% lysozym | + |
| Arginin dihydrolase | − |

DETAILED DESCRIPTION OF THE INVENTION

Figure 1:
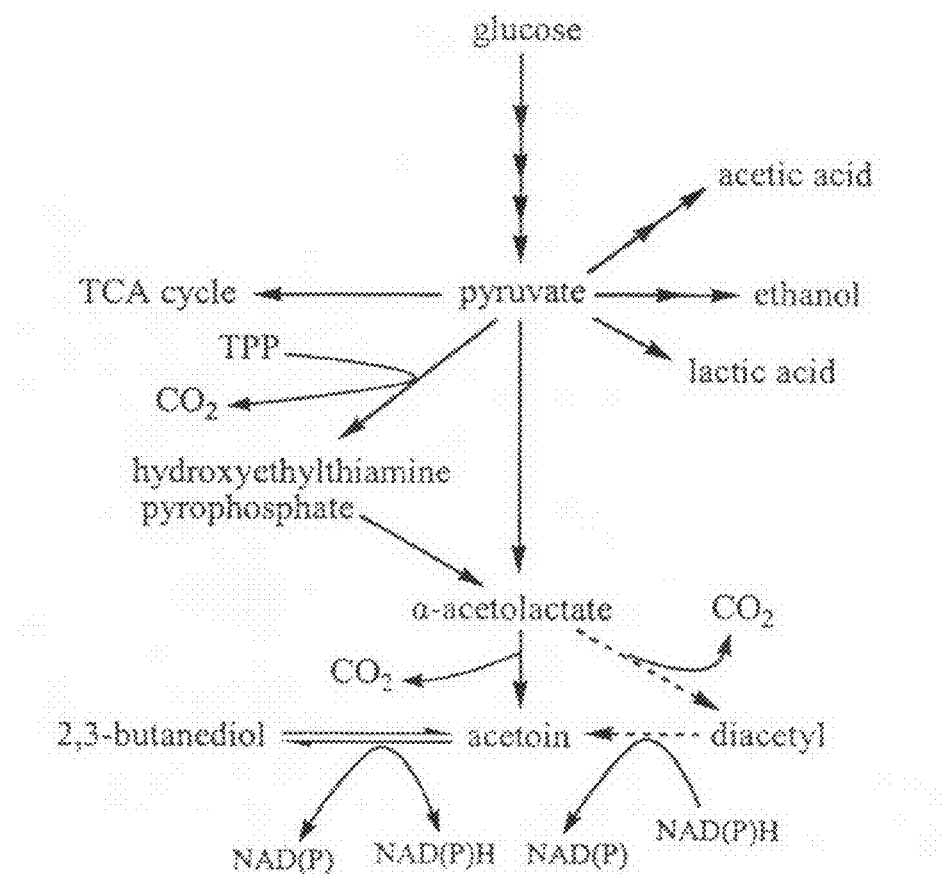
FIG. 1 illustrates the metabolic pathway from glucose to acetoin.
Figure 2:
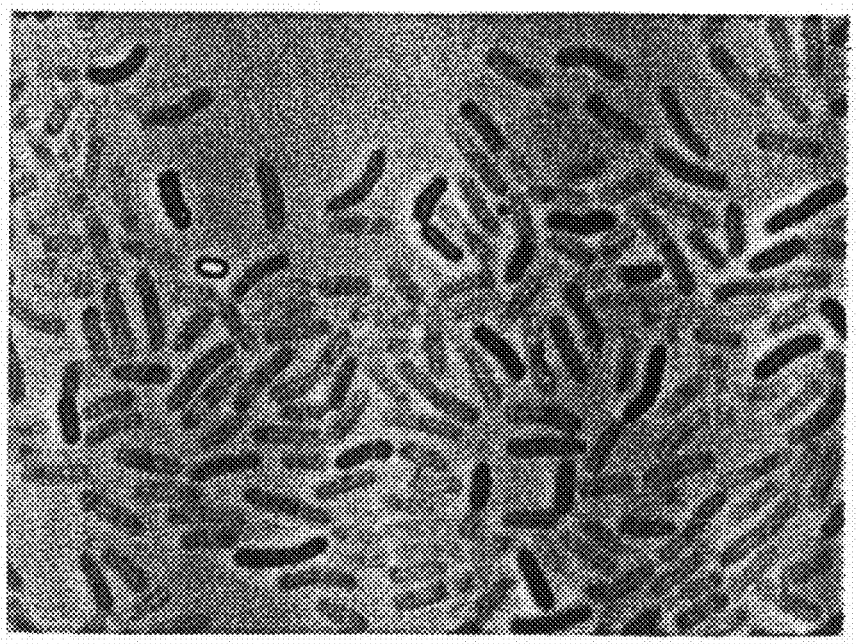
FIG. 2 shows an electron microscope image (2700 fold) of the *Bacillus pumilus* strain XH195 DSM 16187 in the present invention. Electron microscopy was performed in Deutsche Sammlung von Mikroorganismen und Zellkulturen.
Figure 3:
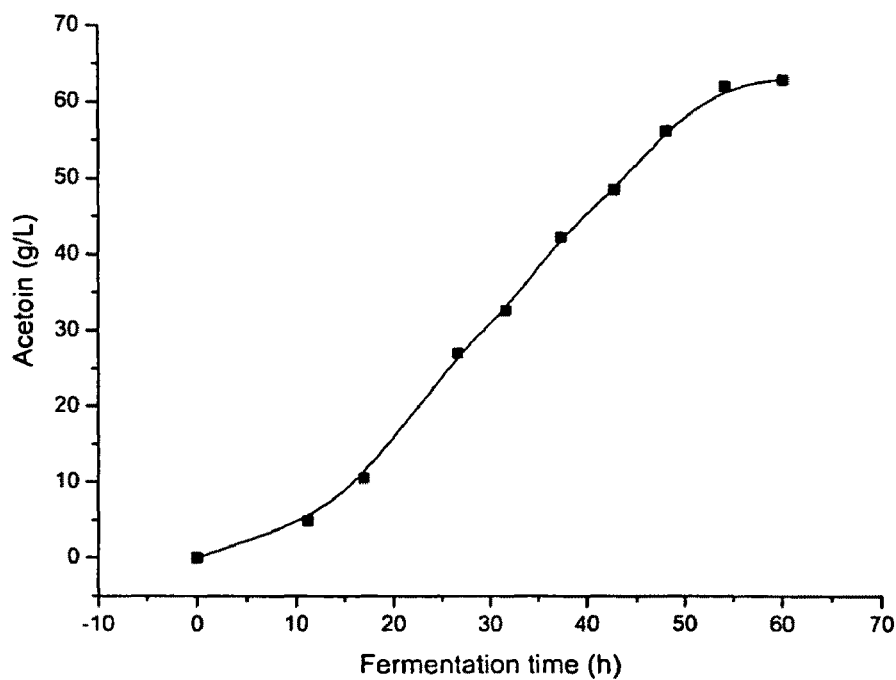
FIG. 3 illustrates the time course of acetoin production by *Bacillus pumilus* XH195 DSM 16187 in the glucose fermentation medium.
Figure 4:
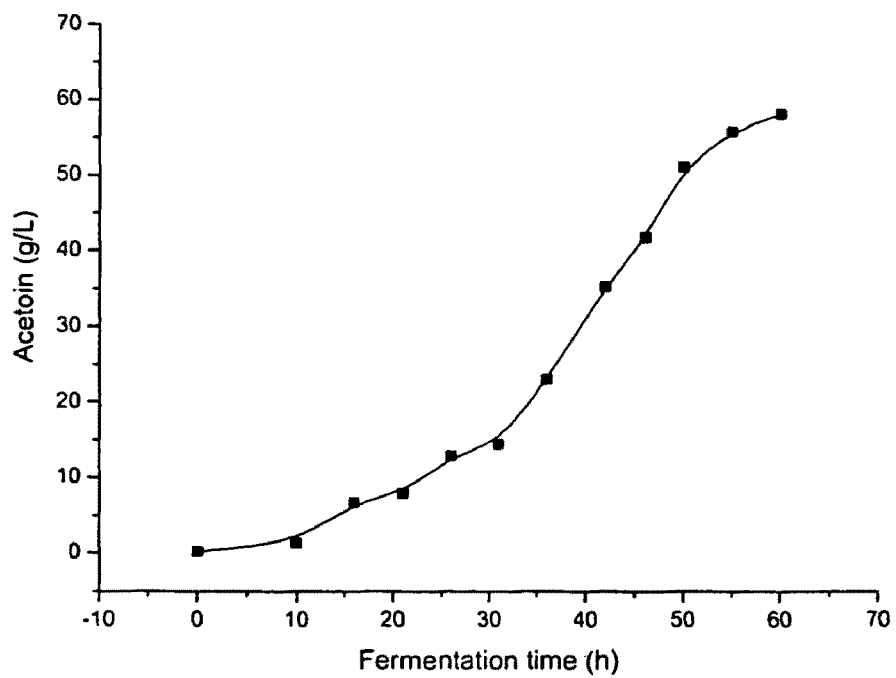
FIG. 4 illustrates the time course of acetoin production by *Bacillus pumilus* XH195 DSM 16187 in the sucrose fermentation medium.

The *Bacillus pumilus* strain XH195 DSM 16187 has the typical fatty acid profile of *Bacillus*.

The 16S rDNA sequence of *Bacillus pumilus* XH195 DSM 16187 is 98.7%~100% similar to those of other *Bacillus pumilus* strains.

The *Bacillus pumilus* strain XH195 DSM 16187 is able to grow in high osmotic LB medium (LB medium containing a high concentration of sugar, LBS).

Each liter of LBS contained 200 g of glucose, 10 g of peptone, 5 g of yeast extract, and 10 g of NaCl. To prepare solid LBS medium, twenty grams of agar was added per liter of LBS. The medium was sterilized at 121° C. for 15 min.

The *Bacillus pumilus* strain XH195 DSM 16187 is used in fermentative production of acetoin.

When *Bacillus pumilus* XH195 DSM 16187 is used to produce acetoin with the glucose fermentation medium or sucrose fermentation medium, fermentation is carried out at 30° C.~40° C. The bacteria were incubated in 50 ml of fermentation medium in 300 ml conical flasks on a shaker at the speed of 160 r/min~220 r/min for 40 h~70 h to obtain mature acetoin fermentation broth.

The above-mentioned glucose fermentation medium contained 1 L of distilled water, 200 g of glucose, 50 g of NH$_4$Cl, 0.50 g of KH$_2$PO$_4$, 4.0 g of K$_2$HPO$_4$.3H$_2$O, 2.0 ml of 10 g/L CaCl$_2$ solution, 2.0 ml of 100 g/L MgCl$_2$.6H$_2$O solution, 200 μl of 10 g/L FeCl$_3$ solution, 200 μl of 50 g/L NaCl solution, 5.0 ml of 10 g/L yeast extract solution, 5.0 ml of metal ions mixture solution (see below), and 200 μl of vitamin mixture solution (see below). The medium was sterilized at 121° C. for 15 min.

The above-mentioned metal ions mixture solution contained 1 L of distilled water, 0.50 g of ZnCl$_2$, 0.50 g of FeCl$_3$, 0.50 g of MnCl$_2$.4H$_2$O, 0.10 g of NaMoO$_4$.2H$_2$O, 0.050 g of CuCl$_2$.2H$_2$O, 0.050 g of Na$_2$WO$_4$.2H$_2$O, and 120 mmol/L of HCl.

The above-mentioned vitamin mixture solution contained 1 L of distilled water, 0.40 g of calcium pantothenate, 0.20 g of inositol, 0.40 g of nicotinic acid, 0.40 g of VB$_6$, 0.20 g of p-aminobenzoic acid, and 0.5 mg of VB$_{12}$.

The above-mentioned sucrose fermentation medium was the same as the glucose fermentation medium, except that 200 g of glucose was replaced with 180 g of sucrose.

The bacteria of *Bacillus pumilus* XH195 DSM 16187 were inoculated in 50 ml of the glucose fermentation medium in 300-ml conical flasks and incubated on a shaker at 180 r/min and 37° C. The concentration of acetoin in the broth reached 63.0 g/L at 60 h.

The bacteria of *Bacillus pumilus* XH195 DSM 16187 were inoculated in 50 ml of the sucrose fermentation medium in 300-ml conical flasks and incubated on a shaker at 180 r/min and 37° C. The concentration of acetoin in the broth reached 58.1 g/L at 60 h.

The acetoin product in the fermentation broth can be extracted using conventional methods and has optical activity.

The present invention overcomes the bottleneck of fermentative production of acetoin by providing the high-yield, acetoin-producing *Bacillus pumilus* strain XH195 DSM 16187. All other strains as mentioned in BACKGROUND OF THE INVENTION have the shortcomings of low yield or producing acetoin as a by-product of 2,3-butanediol biosynthesis, and are difficult to use for industrial-scale production.

The present invention provides a method for acetoin fermentative production, which has the advantages of low-cost starting materials, mild reaction conditions, high acetoin yield (63.0 g/L in flask fermentation), and simple product recovery. The acetoin product is natural, optically active, low cost, and environmentally benign.

Example 1

Screening for Acetoin-Producing Bacterial Strains with High Sugar-Tolerance

Soil samples from apple orchards and vineyards were soaked in LB medium containing a high concentration of sugar (LBS) for over 24 hours, and 50 ml of the resulting soaking solution was incubated in a 300 ml conical flask at 37° C. for 48 hours with shaking at 180 r/min. The culture was diluted $10^2$ and $10^3$ fold, plated on solid LBS plates, and incubated at 37° C. for 24 hours. Single colonies were isolated and cultured to detect acetoin production. Acetoin-producing strains were selected, which were also high-sugar tolerant. One liter of LBS contained 200 g of glucose, 10 g of peptone, 5 g of yeast extract, and 10 g of NaCl. To prepare solid LBS, 20 g of agar was added per liter of LBS. The medium was sterilized at 121° C. for 15 min.

Example 2

Obtaining the Strain of the Present Invention by Mutagenesis

A loop of the bacteria of the strain isolated in EXAMPLE 1 was transferred from LBS slant to a 300-ml conical flask containing 50 ml sterilized LBS and incubated at 37° C. for 24 hours with shaking at 180 r/min.

The resulting cell broth was centrifuged for 5 min at 3000 r/min and the supernatant was discarded. The cell pellet was washed and re-suspended with sterilized normal saline. The cell suspension was transferred to a sterilized conical flask containing glass beads to scatter the cells by manual shaking. The cell suspension was then transferred to a filter with filter paper. The unicellular filtrate was collected in test tubes for later use.

One milligram of N-methyl-N'-nitro-N-nitrosoguanidine (NTG) was dissolved in 2 ml of 0.1 mol/L phosphate buffer; 1 ml of the NTG solution was added to 1 ml of the cell suspension described above. After shaking at 37° C. for 30 min, the cell culture was diluted 1000 fold to stop mutagenesis, and further diluted $10^2$, $10^3$, $10^4$, $10^5$ fold to plate on LBS plates. After incubation at 37° C. for 36 hours, single colonies were isolated from the plates and cultured to detect acetoin production. The strain with the highest yield was selected as the strain of the present invention.

The bacteria of the above-mentioned strain are rod-shaped, 1.5 µm to 3.0 µm in length and 0.6 µm to 0.7 µm in diameter. The colony color is yellow or white. The strain can produce spores and displays a positive VP reaction. It can produce acid from glucose, arabinose, xylose, mannitol, or fructose. The strain can also hydrolyze casein, gelatin and Tween 80, utilize citrate, grow in medium containing 100 g/L NaCl, and grow at 50° C. The strain has the typical fatty acid profile of *Bacillus*. Its 16S rDNA sequence shares 98.7%~100% similarity with those of other *Bacillus pumilus* strains.

The strain of the present invention was named as *Bacillus pumilus* XH195 and has been deposited in Deutsche Sammlung von Mikroorganismen und Zellkulturen on 27 Jan. 2004. The deposit number is DSM 16187.

Example 3

Preparation of Cell Broth of *Bacillus pumilus* XH195 DSM 16187

A loop of bacteria of the *Bacillus pumilus* strain XH195 DSM 16187 cultured on LBS slant was inoculated in a 300-ml conical flask containing 50 ml sterilized LBS and incubated at 37° C. with shaking at 180 r/min for 24 hours to prepare cell broth.

Example 4

Preparation of Mature Acetoin-Producing Fermentation Broth Using Glucose Fermentation Medium The cell broth prepared according to EXAMPLE 3 was inoculated at a volume ratio of 50 ml per liter in 300-ml conical flasks, each of which contained 50 ml of sterilized glucose fermentation medium. The bacteria were cultured at 37° C. with shaking at 180 r/min. Samples were taken every 4 hours to measure the acetoin concentration. The concentration of acetoin reached 63.0 g/L at 60 h, when the flasks were removed from the shaker to stop fermentation, resulting in mature acetoin-producing fermentation broth.

The above-mentioned glucose fermentation medium contained 1 L of distilled water, 200 g of glucose, 50 g of $NH_4Cl$, 0.50 g of $KH_2PO_4$, 4.0 g of $K_2HPO_4.3H_2O$, 2.0 ml of 10 g/L of $CaCl_2$ solution, 2.0 ml of 100 g/L of $MgCl_2.6H_2O$ solution, 200 µl of 10 g/L of $FeCl_3$ solution, 200 µl of 50 g/L of NaCl solution, 5.0 ml of 10 g/L of yeast extract solution, 5.0 ml of metal ions mixture solution, and 200 µl of vitamin mixture solution. The medium was sterilized at 121° C. for 15 min.

The above-mentioned metal ions mixture solution contained 1 L of distilled water, 0.50 g of $ZnCl_2$, 0.50 g of $FeCl_3$, 0.50 g of $MnCl_2.4H_2O$, 0.10 g of $NaMoO_4.2H_2O$, 0.050 g of $CuCl_2.2H_2O$, 0.050 g of $Na_2WO_4.2H_2O$, and 120 mmol/L of HCl.

The above-mentioned vitamin mixture solution contained 1 L of distilled water, 0.40 g of calcium pantothenate, 0.20 g of inositol, 0.40 g of nicotinic acid, 0.40 g of $VB_6$, 0.20 g of p-aminobenzoic acid, and 0.5 mg of $VB_{12}$.

Example 5

Altering Fermentation Conditions to Obtain Mature Acetoin-Producing Fermentation Broth of *Bacillus pumilus* XH195 DSM16187 Using Glucose Fermentation Medium The fermentation step of EXAMPLE 4 was performed at the temperature of 30° C. and shaking speed of 220 r/min. The concentration of acetoin reached 53.2 g/L at 70 h.

Example 6

Altering Fermentation Conditions to Obtain Mature Acetoin-Producing Fermentation Broth of *Bacillus pumilus* XH195 DSM16187 Using Glucose Fermentation Medium The fermentation step of EXAMPLE 4 was performed at the temperature of 40° C. and shaking speed of 160 r/min. The concentration of acetoin reached 55.7 g/L at 40 h.

Example 7

Altering Fermentation Conditions to Obtain Mature Acetoin-Producing Fermentation Broth of *Bacillus pumilus* XH195 DSM16187 Using Sucrose Fermentation Medium The fermentation step of EXAMPLE 4 was performed with the sucrose fermentation medium instead of the glucose fermentation medium. The concentration of acetoin reached 58.1 g/L at 60 h.

The above-mentioned sucrose fermentation medium was the same as the glucose fermentation medium of EXAMPLE 4, except that 200 g of glucose was replaced with 180 g of sucrose.

Example 8

Altering Fermentation Conditions to Obtain Mature Acetoin-Producing Fermentation Broth of *Bacillus pumilus* XH195 DSM16187 Using Sucrose Fermentation Medium The fermentation step of EXAMPLE 7 was performed at the temperature of 33° C. and shaking speed of 200 r/min. The concentration of acetoin reached 54.1 g/L at 68 h.

Example 9

Altering Fermentation Conditions to Obtain Mature Acetoin-Producing Fermentation Broth of *Bacillus pumilus* XH195 DSM16187 Using Sucrose Fermentation Medium The fermentation step of EXAMPLE 7 was performed at the temperature of 40° C. and shaking speed of 170 r/min. The concentration of acetoin reached 55.1 g/L at 45 h.

What is claimed is:

1. An isolated *Bacillus pumilus* strain designated XH195, which is deposited as DSM 16187 in Deutsche Sammlung von Mikroorganismen und Zellkulturen.

2. The isolated *Bacillus pumilus* strain of claim 1, which is capable of producing acetoin by fermentation of a sugar substrate.

3. A method for producing acetoin, comprising:
   (a) providing an isolated *Bacillus pumilus* strain designated XH195, which is deposited as DSM 16187 in Deutsche Sammlung von Mikroorganismen und Zellkulturen;
   (b) introducing the bacterial strain into a fermentation medium;
   (c) allowing fermentation to proceed; and
   (d) obtaining acetoin from a mature acetoin fermentation broth.

4. The method of claim 3, wherein the fermentation medium comprises a sugar substrate.

5. The method of claim 4, wherein the sugar substrate is glucose or sucrose.

6. The method of claim 5, wherein the sugar substrate is glucose.

7. The method of claim 5, wherein the sugar substrate is sucrose.

8. The method of claim 3, wherein the fermentation is allowed to proceed at about 30° C. to about 40° C.

9. The method of claim 3, wherein the fermentation is allowed to proceed for about 40 to about 70 hours.

10. The method of claim 3, wherein the fermentation medium comprises 200 g glucose.

11. The method of claim 10, wherein the fermentation medium further comprises 50 g $NH_4Cl$, 0.5 g $KH_2PO_4$, 4 g $K_2HPO_4$, 2 ml of 1% (w/w) $CaCl_2$, 2 ml of 10% (w/w) $MgCl_2.6H_2O$, 200 μl of 1% (w/w) $FeCl_3$, 200 μl of 5% (w/w) NaCl, 5 ml of 1% (w/w) yeast extract, 200 μl vitamin mixture solution, and 5 μl metal ions mixture solution per liter distilled water.

12. The method of claim 11, wherein the metal ions mixture solution comprises 0.5 g $ZnCl_2$, 0.5 g $FeCl_2$, 0.5 g $MnCl_2.4H_2O$, 0.1 g $Na_2MoO_4.2H_2O$, 0.05 g $CuCl_2.2H_2O$, 0.05 g $Na_2WO_42H_2O$, 120 mmol/L of HCl per liter distilled water.

13. The method of claim 11, wherein the vitamin mixture solution comprises 400 mg of calcium pantothenate, 200 mg of inositol, 400 mg of niacin, 400 mg of pyridoxine hydrochloride, 200 mg of p-aminobenzoic acid, and 0.5 mg of cyanocobalamin per liter of distilled water.

14. The method of claim 3, wherein the fermentation medium comprises 180 g of sucrose.

15. The method of claim 14, wherein the fermentation medium further comprises 50 g of $NH_4Cl$, 0.5 g of $KH_2PO_4$, 4 g of $K_2HPO_4$, 2 ml of 1% (w/w) $CaCl_2$, 2 ml of 10% (w/w) $MgCl_2.6H_2O$, 200 μl of 1% (w/w) $FeCl_3$, 200 μl of 5% (w/w) NaCl, 5 ml of 1% (w/w) yeast extract, 200 μl of vitamin mixture solution, and 5 ml of metal ions mixture solution per liter of distilled water.

16. The method of claim 15, wherein the metal ions mixture solution comprises 0.5 g of $ZnCl_2$, 0.5 g of $FeCl_2$, 0.5 g of $MnCl_2.4H_2O$, 0.1 g of $Na_2MoO_4.2H_2O$, 0.05 g of $CuCl_2.2H_2O$, 0.05 g of $Na_2WO_4.2H_2O$, and 120 mmol/L of HCl per liter of distilled water.

17. The method of claim 15, wherein the vitamin mixture solution comprises 400 mg of calcium pantothenate, 200 mg of inositol, 400 mg of niacin, 400 mg of pyridoxine hydrochloride, 200 mg of p-aminobenzoic acid, and 0.5 mg of cyanocobalamin per liter of distilled water.

* * * * *

UNITED STATES PATENT AND TRADEMARK OFFICE
CERTIFICATE OF CORRECTION

PATENT NO.       : 8,158,402 B2
APPLICATION NO.  : 11/667567
DATED            : April 17, 2012
INVENTOR(S)      : Ping Xu et al.

Page 1 of 1

It is certified that error appears in the above-identified patent and that said Letters Patent is hereby corrected as shown below:

On the Title Page, after Item (65), the Prior Publication Data, and before Item (51), the "Int. Cl." data, insert the following missing data:
--(30)           Foreign Application Priority Data
  Nov. 19, 2004         (CN)......................200410084381.2--.

In claim 11, column 8, line 30, "$MgCl_2.6H_2O$," should read --$MgCl_2 \cdot 6H_2O$,--.

In claim 12, column 8, line 36,
"$MnCl_2.4H_2O$, 0.1 g $Na_2MoO_4.2H_2O$, 0.05 g $CuCl_2.2H_2O$,"
should read
--$MnCl_2 \cdot 4H_2O$, 0.1 g $Na_2MoO_4 \cdot 2H_2O$, 0.05 g $CuCl_2 \cdot 2H_2O$,--.

In claim 15, column 8, line 49, "$MgCl_2.6H_2O$," should read --$MgCl_2 \cdot 6H_2O$,--.

In claim 16, column 8, line 55,
"$MnCl_2.4H_2O$, 0.1 g of $Na_2MoO_4.2H_2O$," should read
--$MnCl_2 \cdot 4H_2O$, 0.1 g of $Na_2MoO_4 \cdot 2H_2O$,--.

In claim 16, column 8, line 56,
"$CuCl_2.2H_2O$, 0.05 g of $Na_2WO_4.2H_2O$," should read
--$CuCl_2 \cdot 2H_2O$, 0.05 g of $Na_2WO_4 \cdot 2H_2O$,--.

Signed and Sealed this
Thirty-first Day of July, 2012

David J. Kappos
*Director of the United States Patent and Trademark Office*